United States Patent
Gerlach et al.

(10) Patent No.: US 12,251,442 B2
(45) Date of Patent: *Mar. 18, 2025

(54) SALICYLIC ACID GEL

(71) Applicant: VANTAGE SPECIALTY INGREDIENTS, INC., Gurnee, IL (US)

(72) Inventors: Chris Gerlach, Buford, GA (US); Michael Davies, Dacula, GA (US)

(73) Assignee: Vantage Specialty Ingredients, Inc., Warren, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/832,171

(22) Filed: Mar. 27, 2020

(65) Prior Publication Data

US 2020/0316206 A1 Oct. 8, 2020

Related U.S. Application Data

(63) Continuation of application No. 15/688,560, filed on Aug. 28, 2017, now abandoned, and a continuation of application No. 14/454,886, filed on Aug. 8, 2014, now abandoned, which is a continuation of application No. 13/789,780, filed on Mar. 8, 2013, now Pat. No. 8,828,979.

(60) Provisional application No. 61/615,956, filed on Mar. 27, 2012.

(51) Int. Cl.
| | | |
|---|---|---|
| A61K 47/18 | (2017.01) | |
| A61K 8/04 | (2006.01) | |
| A61K 8/368 | (2006.01) | |
| A61K 8/41 | (2006.01) | |
| A61K 8/42 | (2006.01) | |
| A61K 9/00 | (2006.01) | |
| A61K 9/06 | (2006.01) | |
| A61K 31/60 | (2006.01) | |
| A61Q 5/00 | (2006.01) | |
| A61Q 5/02 | (2006.01) | |
| A61Q 19/00 | (2006.01) | |

(52) U.S. Cl.
CPC .............. *A61K 47/18* (2013.01); *A61K 8/042* (2013.01); *A61K 8/368* (2013.01); *A61K 8/41* (2013.01); *A61K 8/42* (2013.01); *A61K 9/0014* (2013.01); *A61K 9/06* (2013.01); *A61K 31/60* (2013.01); *A61Q 5/006* (2013.01); *A61Q 5/02* (2013.01); *A61Q 19/00* (2013.01); *A61K 2800/52* (2013.01)

(58) Field of Classification Search
None
See application file for complete search history.

(56) References Cited

U.S. PATENT DOCUMENTS

| | | | | |
|---|---|---|---|---|
| 5,505,949 | A * | 4/1996 | Benitez ................. | A61K 8/368 424/401 |
| 5,558,871 | A * | 9/1996 | Griat ..................... | A61K 8/922 424/401 |
| 5,587,154 | A * | 12/1996 | Dowell .................. | A61K 8/20 424/70.11 |
| 2006/0239953 | A1* | 10/2006 | Clapp .................... | A61K 8/92 424/70.22 |

\* cited by examiner

*Primary Examiner* — Patricia Duffy
*Assistant Examiner* — Garen Gotfredson
(74) *Attorney, Agent, or Firm* — Louis C. Paul & Assoc.

(57) ABSTRACT

A concentrated salicylic acid gel comprising salicylic acid and a stabilizer compound, wherein the salicylic acid comprises at least 30 wt % of the total weight of the gel.

9 Claims, No Drawings

SALICYLIC ACID GEL

CROSS-REFERENCE OF RELATED APPLICATIONS

This application is a continuation of U.S. application Ser. No. 15/688,560, filed Aug. 28, 2017 (now pending), which is a continuation of U.S. application Ser. No. 14/454,886, filed Aug. 8, 2014, (now abandoned), which application is a continuation of U.S. application Ser. No. 13/789,780, filed Mar. 8, 2013, (now U.S. Pat. No. 8,828,979, issued Sep. 9, 2014), which claims priority to U.S. Provisional Application Ser. No. 61/615,956 filed on Mar. 27, 2012. All applications are hereby incorporated by reference in their entirety.

FIELD OF THE INVENTION

The invention relates to a concentrated gel of salicylic acid, and products produced therefrom.

BACKGROUND OF THE INVENTION

Salicylic acid, also known as 2-hydroxybenzenecarboxylic acid, is a monohydroxybenzoic acid. Its salts and esters are known as salicylates. Salicylic acid has the formula:

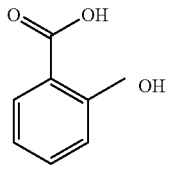

Salicylic acid is also known for providing pain relief when applied as a liniment, for example Salicylic acid is used in many skin-care products. For example, salicylic acid is well known for its use in anti-acne treatments. In addition to the treatment of acne, salicylic acid is also used in products for treatment of psoriasis, calluses, corns, keratosis pilaris, and warts. It works as a keratolytic, bacteriocide and comedolytic agent. Salicylic acid is also used in shampoos for treatment of dandruff and as a chemical exfoliant.

Salicylic acid can cause burns if applied in high concentrations. Typically, over-the-counter limits are 2% for topical treatments (that remain on the skin) and 3% for cleansers or shampoo (products that are washed off.) Higher concentrations (e.g. up to 40 wt %) may be used for wart removal but should be applied cautiously and only to the wart and not the surrounding skin.

Salicylic acid is poorly soluble in water. It is therefore difficult to prepare solutions of salicylic acid that remain precipitate-free.

BRIEF SUMMARY OF THE INVENTION

The present invention is directed to a concentrated salicylic acid gel comprising salicylic acid and a stabilizer compound, wherein the salicylic acid comprises at least 30 wt % of the total weight of the gel.

The present invention is further directed to a dilute salicylic acid solution comprising the concentrated salicylic acid gel and a solvent wherein the concentration of the salicylic acid in the solution is 25 wt % or less.

The present invention is further directed to products prepared with the concentrated salicylic acid gel or with dilute solution of the gel in water.

In one aspect the salicylic acid gel is combined with ingredients to form a body or hand lotion. In another aspect the salicylic acid gel is combined with ingredients to form an anti-dandruff shampoo. In yet another aspect the salicylic acid gel is combined with ingredients to form wart medication. In yet another aspect the salicylic acid gel is combined with ingredients to form an anti-acne medication.

DETAILED DESCRIPTION OF THE INVENTION

Aspects of the invention are directed to a concentrated gel of salicylic acid and at least one stabilizer compound selected from nitrogen compounds.

The concentrated gel comprises at least 30 wt % salicylic acid, for example 30 wt % to 60 wt %, or 40 to 55 wt % salicylic acid, based on total weight of the gel.

The concentrated gel comprises the stabilizer compound in an amount of 40 to 70 wt %, or 45 to 60 wt %, which is an amount effective to provide stability to the salicylic acid in the gel.

The concentrated salicylic acid gel is formed by mixing salicylic acid with the stabilizer compound until the salicylic acid is dissolved in the stabilizer compound. No water or solvent such as ethanol is included in the gel. There are only two components that form the gel: the stabilizer compound (complexing agent) and the salicylic acid.

The mixing of the salicylic acid and the stabilizer compound may be done at room temperature. Alternatively the mixing may occur at an elevated temperature such as up to 50° C. Generally mixing takes about 30 to 120 minutes.

The concentrated gel may then be stored for future use. Since the gel contains very concentrated salicylic acid, less storage space is required than dilute solutions of salicylic acid.

The stabilizer compound may be any suitable nitrogen compound that stabilizes the salicylic acid in the concentrated gel. Nitrogen compounds useful to form the highly concentrated salicylic gel include, but not limited to, alkoxylated amides, alkoxylated amines, alkyl-substituted amino acids, alkylamido alkylamines, amides, amine oxides, amines, and betaines. Ideally, a clear product should be produced.

In one aspect, the nitrogen compound is cocamidopropyl dimethylamine. The cocamidopropyl dimethylamine is particularly suitable for high concentrations of salicylic acid. When diluted in water, the resulting solution is stable and clear.

The concentrated gel can be diluted to any suitable level for use. Dilution of the salicylic acid gel may occur by the addition of water, a short chain alcohol such as ethanol and isopropanol, or any combination thereof. Upon dilution, the salicylic acid forms a clear, stable solution in the water or alcohols—that is, the salicylic acid does not precipitate out.

For pH evaluation, 95% water was added to 5% of the gel resulting in a 2% salicylic acid concentration; the maximum allowed for anti-acne products. The same evaluation was run using 92.5% water and 7.5% of the gel (3% active salicylic acid; the maximum allowed for anti-dandruff products) and 40% water and 60% of the gel to evaluate for the wart remover monograph. All of these studies resulted in clear, stable solutions with pH levels between 3 and 4.

The pH of the dilute system is generally less than 5, such as 2 to 5, 2.5 to 4.5, typically 3 to 4.

For topical purposes, the dilute system must pass the USP Monograph for a Salicylic Gel which includes an assay for salicylic acid.

The diluted product may be combined with other suitable ingredients to form the final products such as creams, lotions, make-ups, toners, astringents, skin cleansing compositions, shampoos, and conditioners. These compositions contain about 0.1-40 wt % of salicylic acid. The amount of salicylic acid in the final product depends on the intended purpose of the product.

Ciis typically contain about 10-90 wt % water and 10-90 wt % oil. Creams may also contain humectants, emollients, surfactants, emulsifiers, preservatives and fragrances. Creams would generally contain from 0.1 to 5 wt % salicylic acid.

L4a-t[99s typically contain 20-80 wt % oil and 10-80 wt % water in an emulsion form. In addition, lotions may contain humectants, emollients, surfactants, fragrances, preservatives and so forth. Creams would generally contain from 0.2 to 5 wt % salicylic acidke-ups typically contain about 5-70 wt % oil, 10-95 wt % water, and about 5-40 wt % pigment. In addition, the makeup may contain surfactants, silicones as part of the oil phase, humectants, emollients, preservatives, fragrances, etc. Make-up would generally contain from 0.1 to 3 wt % salicylic acid.

Anti-dandruff shampoos typically contain 1-40 wt % of a cleansing surfactant and 1090 wt % water. The shampoo may also contain any one of ingredients such as surfactants, colorants, preservatives, fragrance, emulsifiers, viscosity adjusters, and conditioning agents. Anti-dandruff shampoos would generally contain from 0.18 to 3 wt % salicylic acid.

Hair conditioners typically contain include 10-95 wt % water, 0.5-30 wt % conditioning ingredients such as quaternary ammonium compounds or amphoteric polymers, proteins, etc., and 1-40% surfactants. Hair conditioners may also contain volatile or nonvolatile silicones. Hair conditioners would generally contain from 0.1 to 4 wt % salicylic acid.

Toners typically contain about 0-85 wt % alcohol, 0.01-5 wt % surfactant, and 0.1-5 wt % humectants, 0.1-85% water.

The salicylic acid may also be used in ointments, gels, or solutions. Suitable ointments are hydrophilic ointments (USP) or petroleum.

The amount of salicylic acid present in the final product depends on the product. For example, acne treatment products generally contain 0.5 to 2 wt % salicylic acid, dandruff and seborrheic dermatitis, and psoriasis treatment products generally contain 3 wt % salicylic acid, and wart treatments generally contain up to 40 wt % salicylic acid, typically 5 wt % to 40 wt % or 17 wt % to 25 wt %.

Example 1

A 40% salicylic acid was blended with 60% cocamidopropyl dimethylamine. The resulting concentrated gel was slightly viscous, clear, and yellow.

The concentrated gel was diluted to 2 wt % active salicylic acid in water and separately in ethanol. The resulting solutions were clear and colorless. No precipitate was formed either in water or in ethanol. The pH of the water solution was approximately 3.2.

Stability tests were then performed on the water solution. The concentrated gel and the diluted 2 wt % active salicylic acid solution were prepared and subjected to accelerated stability protocol which consisted of five freeze/thaw cycles and two weeks in a 50° C. oven. Under both of these conditions there were no significant changes to either sample. The samples that were frozen were obviously solid when removed from the freezer and the 50° C. samples were less viscous. In both cases, when the samples returned to room temperature, they were essentially identical to the control samples. There was no color or viscosity change and no precipitate was formed.

The gel was also diluted to 25 wt % active salicylic acid in water. The resulting solution was a slightly viscous, yellow, clear solution. No precipitate was formed. A physical accelerated stability test was run on this prototype consisting of samples be held at 50° C. for two weeks and another sample run through five freeze/thaw cycles. Under both of these conditions there were no physical changes to the product include pH, viscosity, color and appearance.

Example 2

A lotion was prepared with 5% of the gel of example 1 in 91% water with 4% Egel 305 [Polyacrylamide (&) C12-13 isoparaffin (&) Laureth-7]. The result was a white lotion that would be applicable for an anti-acne product. It underwent the same accelerated stability testing as mentioned above (50° C. for 2 weeks and 5 freeze/thaw cycles); there were no significant physical changes to the product during the stability testing.

Example 3

An anti-dandruff shampoo was prepared containing 3 wt % salicylic acid.

|  |  | Percent |
|---|---|---|
|  | Water | 36.50 |
| Active ingredient | Cocamidopropyl Diinethylamine (&) Salicylic Acid (Curcylic ® 40) | 7.50 |
| Surfactant blend | PEG-80 Sorbitan Laurate (&) Cocamidopropyl Betaine (&) Sodium Trideceth Sulfate (&) Glycerin (&) Disodium Lauroamphodiacetate (&) PEG-150 Distearate (&) Sodium Laureth-13 Carboxylate (Sulfochem ™ B-NBB) | 50.00 |
| Thickener | PEG-120 Methyl Glucose Trioleate (&) Propylene Glycol (&) Water (Glucamate ™ LT) | 5.00 |
| Preservative | Propylene Glycol (&) Diazolidinyl Urea (&) Methylparaben (&) Propylparaben (Nipaguard PDU) | 1.00 |
|  | Citric Acid | qs to pH 4 |
|  |  | 100.00% |

In an appropriate container, water, and Curcylic®40 were mixed until uniform. Sulfochem B-NBB, Glucamate LT and Nipaguard PDU were added and mixed until homogenous. Then citric acid was added, with continued mixing, until the batch reached pH of approximately 4.0. Viscosity: >1300 cp. Stability: Passed 2 weeks 50° C.; 5 Freeze/Thaw cycles.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

We claim:

1. An anhydrous gel concentrate consisting of two hydrophobic constituents, (a) salicylic acid and (b) an alkylamido alkylamine, wherein the ratio a:b is from 3:7 to 3:2, wherein the gel is comprised of at least 30% salicylic acid, wherein upon dilution in water a clear solution is formed having a pH of less than 5 that is visibly free of salicylic acid precipitate.

2. A method for making a topical product containing salicylic acid at a concentration of from about 0.1 wt % to 40 wt % based on the total weight of the topical product comprising the step of adding the anhydrous gel concentrate of claim 1 to a solvent selected from the group consisting of water, ethyl alcohol and isopropyl alcohol.

3. The method of claim 2 wherein the topical product is a cream or lotion that contains salicylic acid at a concentration of up to 5%, based on the total weight of the topical product.

4. The method of claim 2 wherein the topical product is used to treat acne and contains salicylic acid at a concentration of from 0.5% to 2.0% based on the total weight of the topical product.

5. The method of claim 2 wherein the topical product is used to remove warts and contains salicylic acid at a concentration of from 5% to 40% based on the total weight of the topical product.

6. The method of claim 2 wherein the topical product is used to treat dandruff and contains salicylic acid at a concentration of from 1.8% to 3.0% based on the total weight of the topical product.

7. The anhydrous gel concentrate of claim 1 wherein (a) salicylic acid comprises from 30 wt % to 60 wt % of the anhydrous gel concentrate and (b) the alkylamido alkylamine comprises from 40 wt % to 70 wt % of the anhydrous gel concentrate.

8. The anhydrous gel concentrate of claim 7 wherein the ratio of a:b is from 2:3 to 11:9.

9. The anhydrous gel concentrate of claim 7 wherein the alkylamido alkylamine is cocamidopropyl dimethylamine.

* * * * *